(12) United States Patent
Sabini et al.

(10) Patent No.: US 6,663,352 B2
(45) Date of Patent: Dec. 16, 2003

(54) METHOD AND APPARATUS FOR DYNAMICALLY DETERMINING VAPOR PRESSURE IN PUMPING SYSTEMS

(75) Inventors: Eugene P. Sabini, Skaneateles, NY (US); Oakley Henyan, Auburn, NY (US)

(73) Assignee: ITT Manufacturing Enterprises, Inc., Wilmington, DE (US)

( * ) Notice: Subject to any disclaimer, the term of this patent is extended or adjusted under 35 U.S.C. 154(b) by 0 days.

(21) Appl. No.: 09/912,819

(22) Filed: Jul. 25, 2001

(65) Prior Publication Data

US 2003/0021695 A1 Jan. 30, 2003

(51) Int. Cl.[7] ............................................... F04B 49/03
(52) U.S. Cl. ..................... 417/63; 417/87; 417/201; 417/292; 73/730; 73/731; 73/1.71
(58) Field of Search ...................... 417/87, 201, 292, 417/63; 73/730, 731, 1.72, 1.71

(56) References Cited

U.S. PATENT DOCUMENTS

| | | | | |
|---|---|---|---|---|
| 4,381,650 A | * | 5/1983 | Mount | 62/157 |
| 5,318,151 A | * | 6/1994 | Hood et al. | 184/6.1 |
| 6,302,653 B1 | * | 10/2001 | Bryant et al. | 417/53 |
| 6,314,750 B1 | * | 11/2001 | Ishikawa et al. | 62/129 |
| 6,402,479 B1 | * | 6/2002 | Lagedamont et al. | 417/201 |

* cited by examiner

Primary Examiner—Justine R. Yu
Assistant Examiner—Emmanuel Sayoc
(74) Attorney, Agent, or Firm—Ware, Fressola, Van Der Sluys & Adolphson LLP (57) ABSTRACT

A method and system for dynamically determining a vapor pressure of a fluid passing through a pumping system by diverting a portion of the fluid from the pumping system into a chamber, isolating the diverted fluid from the pumping system, evacuating the chamber and measuring the vapor pressure of the isolated fluid. In another aspect of the invention, a temperature compensation device is included in the chamber to alter the chamber fluid temperature to insure that the chamber fluid temperature is substantially the same as the fluid in the pumping system.

12 Claims, 6 Drawing Sheets

METHOD AND APPARATUS FOR DYNAMICALLY DETERMINING VAPOR PRESSURE IN PUMPING SYSTEMS

FIELD OF THE INVENTION

This invention is related to pumps and pumping systems. More specifically, this invention is directed to the dynamic measurement of vapor pressure in pumping systems.

BACKGROUND OF THE INVENTION

In the art of pumps and pumping systems, Net Positive Suction Head Available ($NPSH_a$) pressure is a well-known operating characteristic that is necessary for maintaining proper operation. Maintaining system $NPSH_a$ higher than Net Positive Suction Required ($NPSH_r$) by the pump is critical as it insures a smooth flow of the fluid entering and leaving a pump. $NPSH_a$ conventionally is determined by measuring or estimating known system operating parameters and applying these values in the well-known formula:

$$NPSH_a = (Ps - Pv)/SG + \Delta Zs + hvs \qquad [1]$$

where Ps is pump suction absolute pressure, in feet;

Pv is pumpage vapor pressure, in feet;

SG is pumpage Specific Gravity;

$\Delta Zs$ is the difference in suction gauge height to pump suction input data, in feet; which is positive if gage is above pump datum and negative if gage is below pump datum; and hvs is suction head velocity, in feet.

Conventionally, the measurement of each of the operating parameters is not or cannot be measured as the pump is in operation. Generally, when the parameters are not measured, their values are estimated based on known characteristics, such as pump size, type of fluid, fluid viscosity, temperature, fluid flow rate, etc. In such case, the $NPSH_a$ is statically determined based on the information available when the pump system is set up.

However, conditions within the pumping system can change which can induce significant changes in the operating conditions and alter the actual $NPSH_a$ of the pumping system. For example, cavitation is a well-known problem in pumping systems that can alter the $NPSH_a$. Cavitation occurs when air, in the form of bubbles, is released from the pumped fluid and explode against the high speed pump impeller blades. The exploding air bubbles cause ever increasing damage to the impeller blades and the damaged impeller blades are detrimental to the smooth flow of the pumped fluid. In such cases, additional air bubbles are released from the pump and the cavitation level increases. As the cavitation level increases, the vapor pressure within the pump increases and, from Equation 1 above, the $NPSH_a$ pressure decreases.

However, vapor pressure is not a measurable parameter in the conventional pumping systems. Thus, a change in vapor pressure can occur and the change in actual $NPSH_a$ can cause significant damage to the pumping system or the system that is using the pumped fluid. Hence, there is a need in the art to dynamically measure vapor pressure to be able to determine $NPSH_a$ pressure when the pump is in operation.

SUMMARY OF THE INVENTION

A method and device for dynamically determining a fluid vapor pressure passing through a pumping system is disclosed. The device measures the fluid vapor pressure by diverting a portion of the fluid from the pumping system into a vapor pressure measuring device chamber, isolating the diverted fluid from the pumping system, evacuating the chamber and measuring the vapor pressure of the isolated fluid. In another aspect of the invention, a temperature compensation device can be included in the vapor measuring device chamber to change the temperature of the chamber fluid so the fluid temperature in the chamber is substantially the same as the fluid in the pumping system.

It is to be understood that these drawings are solely for purposes of illustrating the concepts of the invention and are not intended as a level of the limits of the invention. It will be appreciated that the same reference numerals, possibly supplemented with reference characters where appropriate, have been used throughout to identify corresponding parts.

DETAILED DESCRIPTION OF THE PRESENT INVENTION

Figure 1:
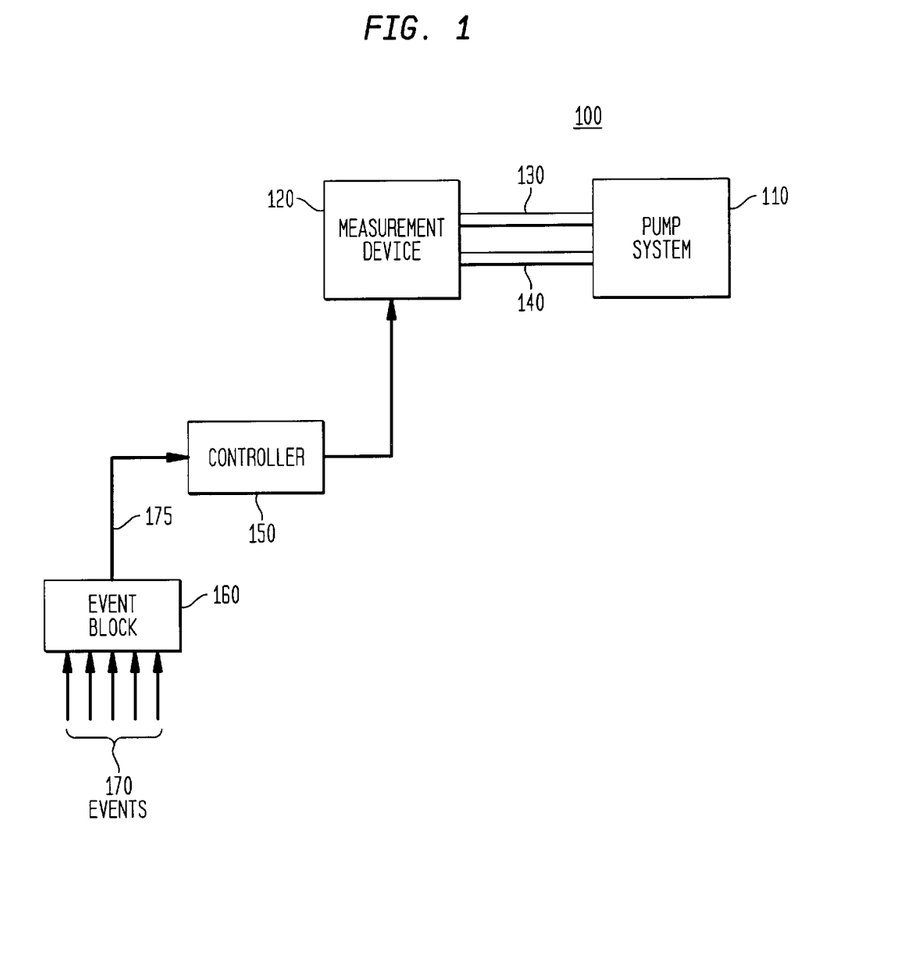
FIG. 1 illustrates a block diagram of an exemplary system in accordance with the principles of the present invention.

FIG. 1 depicts an exemplary system 100 utilizing the principles of the present invention. In this illustrative example, a portion of the pumped fluid is selectively diverted from pump 110 to vapor pressure determination device 120, designated a measurement device, through piping or conduit 130 and returned to pump 110 through piping or conduit 140. Controller 150 controls the process flow of pressure determination device 120. Controller 150 may be any mechanical configuration that controls valves or actuators, or electrical means, such as dedicated or programmable processors, that can initiate a known sequence, which controls valves or actuators. In this illustrative system, controller 150 is responsive to an event indicator, which is represented as Event block 160. Event block 160 further is depicted as receiving a plurality of event indicators 170, which when interpreted by Event block 160 can initiate a vapor pressure measurement through measurement event 175. Controller 150 responsive to measurement event 175 can then initiate the operation of measurement device 120.

Although not illustrated, it will be appreciated that measurement device 120 and controller 150 may be in bi-directional communication over a network, such as the Internet, and pump system 110 may provide information to controller 150 over the same or a different network. Similarly, event indicators 170, which are input to Event block 160 may be any external event, such as a user request, an alarm indication, a predetermined time event, a monitoring signal, a warning indication, etc., or an internal event, for example, an expiration of a known time period. As will further be appreciated, Event block 160, and controller 150 can be included within device 120.

Figure 2:
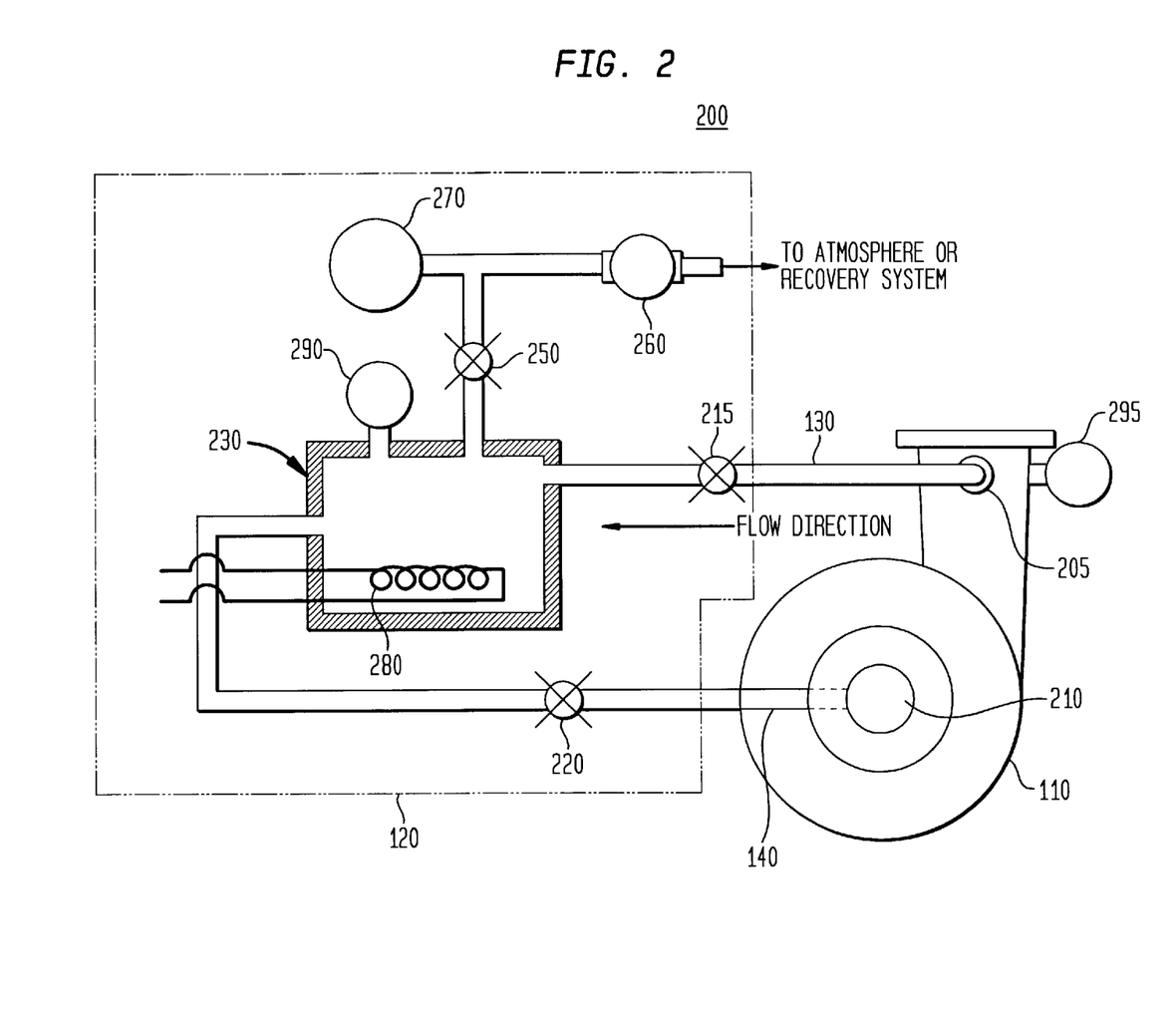
FIG. 2 illustrates an exemplary embodiment of a measurement device in accordance with the principles of the present invention.

FIG. 2 illustrates a block diagram of an exemplary vapor pressure determination device 120 in communication with pump 110. In this illustrative example, fluid is drawn from pump head 205 through pipe or conduit 130 into vapor determination device 120 and returned to pump impeller 210 through pipe or conduit 140. Valve 215 controls the flow of fluid from pump 110 through piping 130 such that when valve 215 is in a closed position fluid is prevented from entering vapor pressure determination device 120. Valve 220 controls the return of fluid from vapor pressure determination device 120 to pump 110. When valves 215 and 220 are in an open position, a small amount of fluid is transferred from pump 110 to device 120 and collected in chamber 230 and fluid accumulated in chamber is returned to pump 110. When valves 215 and 220 are in a closed position, fluid is prevented from returning to pump 110. Hence, this diverted fluid is isolated from the fluid contained in pump 110.

When sufficient fluid has been diverted from pump 110 and collected in chamber 230, valves 215 and 220 are closed and valve 250 is opened. Valve 250 allows fluids, e.g., air or gases, collected in chamber 230 to be drawn by vacuum pump or ejector 260. Vacuum pump 260, which may be turned on before or after valve 250 is opened, is in fluid communication with chamber 230 and begins to pump the air from chamber 230. When the vapor pressure in chamber 230 reaches a steady state value, a pressure measure is recorded on pressure gauge 270.

The air or gases evacuated from chamber 230, by pump 260, in the case of non-toxic fluids, such as water, may be returned to the atmosphere. However, in the case of toxic fluids, the evacuated air or gases are returned to a return tank (not shown). The handling of discarded fluids is well known and need not be discussed in detail herein.

In one embodiment of the invention, measurement device 120 is proximately located to pump 110 such that the fluid temperature in chamber 230 is substantially the same as that of fluid within pump 110. In a preferred embodiment, measure device 120 is attached to pump 110 to minimize the length of piping 130 and 140. In this preferred embodiment, the fluid temperature in pump 110 and in chamber 230 remains substantially the same. However, it will be appreciated that measurement device 120 may be located a substantial distance from pump 110. In this case, optional temperature compensation device 280, e.g., heater, heat exchanger, air conditioner, may be included within chamber 230. Heater 280 can be set such that the temperature of fluid with chamber 230 is substantially the same as the temperature of the fluid within the pump 110.

In another aspect, optional temperature gauge 295 is proximately located with respect to pump 110 to measure temperature of the fluid within pump 110. The measured temperature may then be transmitted over a network, such as a local area network, wide area network, POTS (Poor Old Telephone System) network, or the Internet, to a central control station, for example controller 150 as shown in FIG. 1. Similarly, temperature gauge 290 proximately located with chamber 230 can measure fluid temperature within chamber 230. This measured temperature can also be transmitted to a central station, e.g., controller 150, over the same or a different network. The central station may then compare the measured temperatures and provide control signals to set the optional temperature compensation device 280 in chamber 230 such that the measured temperature of fluid in chamber 230 is substantially the same as the temperature of fluid in pump 110. In this case, the controller may inhibit a measurement until the measured temperatures are substantially the same, as is more fully disclosed with regard to FIG. 4. Accordingly, in the one aspect of the invention, the determination of vapor pressure for pump 110 is compensated for temperature even when chamber 230 is located a substantial distance from pump 110.

Figure 3:
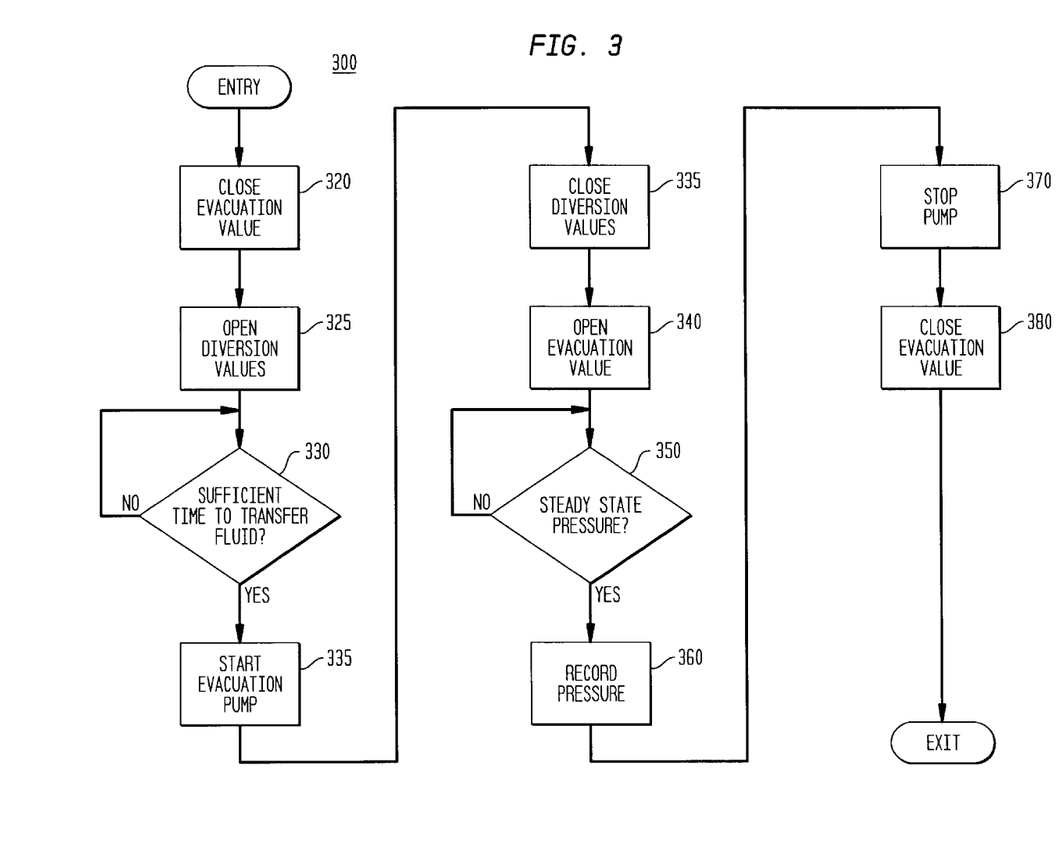
FIG. 3 illustrates a flow chart of an exemplary processing for measuring vapor pressure in accordance with the principles of the present invention.

FIG. 3 illustrates an exemplary processing flow 300 for determining vapor pressure using the components illustrated in FIG. 2 in accordance with the principles of the invention. In this illustrative example, the detection of a known event causes process 300 to be initiated. A known event may be initiated after a predetermined time period, e.g., one per 10 minutes, once per hour, once per day, etc., or may be initiated by an external event, for example, a indication of a change in fluid flow, change in fluid temperature, change in level of fluid cavitation, user initiated request for vapor pressure measurement, etc.

At block 320, evacuation valve 250 is closed and at block 325, diversion valves 215 and 220 are opened. In this configuration a portion of fluid from pump 110 is transferred to chamber 230 and fluid in chamber 230 is returned to pump 110. At block 330, a determination is made, in this illustrative example, whether sufficient time has elapsed to insure that fluid in chamber 230 is representative of the current state of fluid in pump 110. After sufficient time has elapsed, evacuation pump 260 is started at block 335, valves 215 and 220 are closed at block 340 and valve 250 is opened at block 345.

At block 350, a determination is made, in this illustrative example, whether the fluid vapor pressure has achieved a steady state level. When steady state has been achieved, a vapor pressure is measured at block 360. The operation of evacuation pump 260 ceases, at block 370, and valve 250 is then closed at block 380.

Although decisions of process 300 are representatively illustrated on a timed basis, it will be appreciated that other means may be used to control the progression of process 300. For example, the determination at block 330 can be made based on a measure of the transfer of fluid between pump 110 and chamber 230. This measure of fluid may be determined by a fluid flow meter (not shown) which will indicate the amount of fluid transferred. The determination of steady state vapor pressure can be made, for example, by monitoring the change, or rate of change, of vapor pressure and indicating steady state when the change or rate of change is below a known level. The known level may be, for example, a percentage of the absolute pressure level. Hence, steady state vapor pressure can be indicated when the change pressure is, for example, less than a first known percent when absolute pressure is below a known level, and less than a second known percent when absolute pressure in above a known level. This exemplary process of determining steady state vapor pressure may be further refined by incorporating a plurality of known levels and corresponding percentage values.

Figure 4:
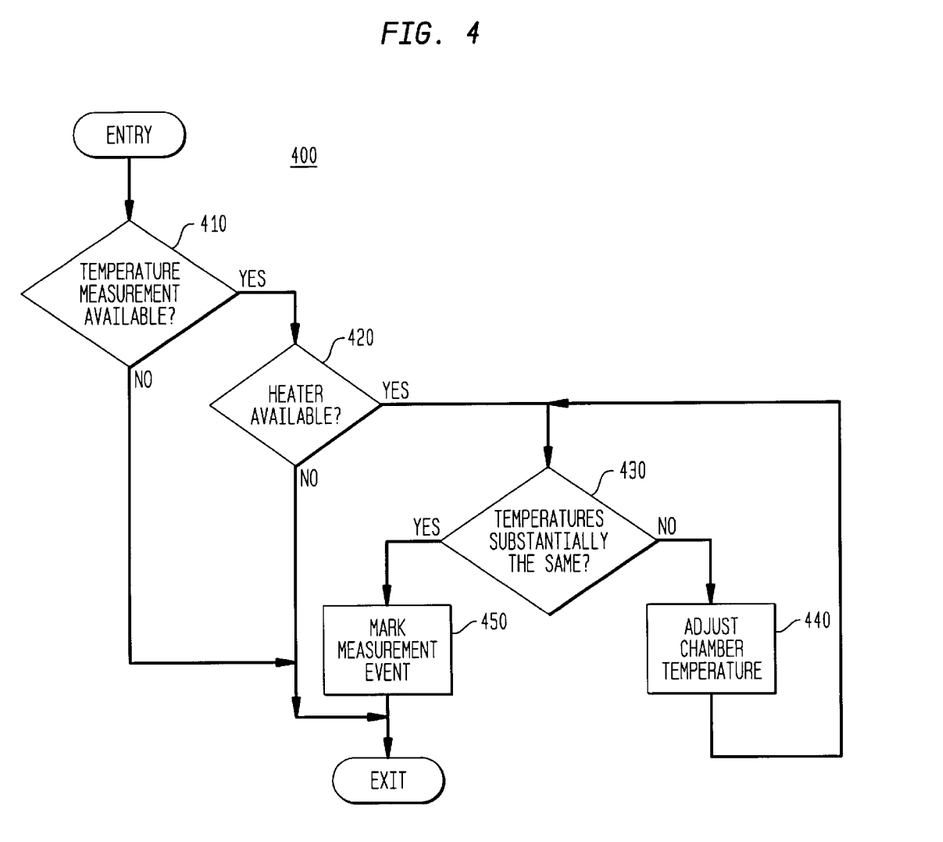
FIG. 4 illustrates a flow chart of an exemplary processing of vapor pressure measurement event in accordance with a second aspect of the invention.

FIG. 4 illustrates an exemplary measurement event initiating process 400. In this exemplary process 400 vapor pressure measurement is taken after it is determined that the temperature of the fluid in pump 110 and chamber 230 are substantially the same. Process 400 can be used as an independent event initiating process or may be used in conjunction with a known measurement initiating event process. In the latter case, the operation of process 400 can be used to insure that a vapor pressure measurement is taken when the temperature of fluid in chamber 230 and pump 110 are substantially the same.

At block 410, a determination is made whether temperature measurements are available. If the answer in the negative, then no further processing is performed by process 400. However, if the answer is in the affirmative, then a determination is made at block 420 whether temperature compensation device 280 is included in device 120. If the answer is in the negative, then no further processing performed by process 400.

However, if the answer is in the affirmative, than a determination is made, at block 430 whether the temperature of fluid in chamber 230 and pump 110 are substantially the same. If the answer is in the affirmative, then a measurement event is indicated and process 400 is completed.

If, however, the answer at block 430 is in negative, then temperature compensation device 280 is adjusted, at block 440 to alter the temperature of fluid in chamber 230. For example, if temperature compensation device 280 is an electrical heater, as illustrated, then the current flow to heater element 280 can be increased to increase the temperature of fluid in chamber 230. Heater element 280 may also be a gas heater using propane gas from example.

Process then returns to block 430 to monitor the fluid temperature in chamber 230. Although not shown, it will be appreciated that a temperature compensation device 280 may be a cooling element, which is used to cool the temperature of fluid in chamber 230.

Figure 5A:
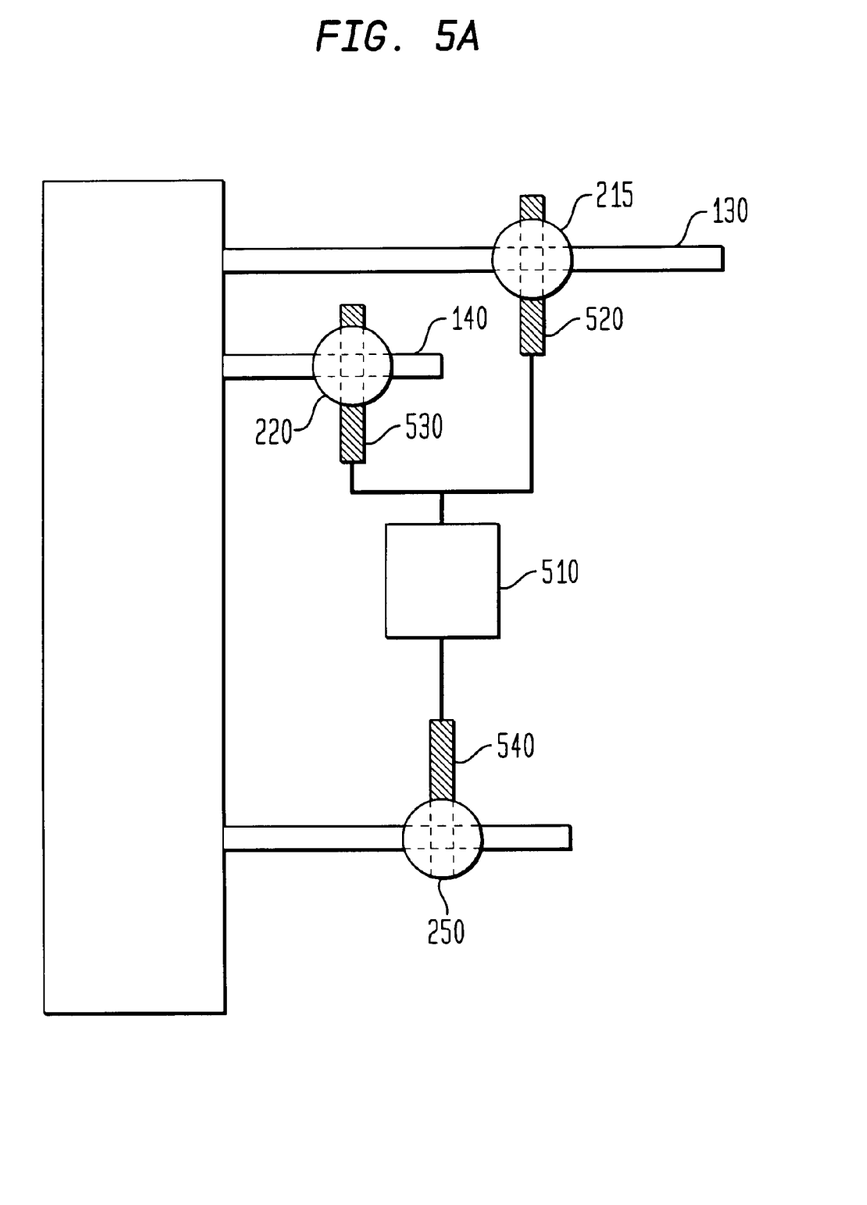
FIGS. 5a and 5b illustrate an exemplary valve operation in accordance with the principles of the invention.

FIG. 5a illustrates an exemplary valve actuating means in accordance with the principles of the invention. In this illustrative example, when actuator 510 is positioned in a first position, solenoids or plungers 520, 530 engage valves 215, 220, respectively, to prevent fluid flow through conduits 130, 140 respectively. Further solenoid or plunger 540 is removed from valve 250 and fluid flow passes through valve 250.

Figure 5B:
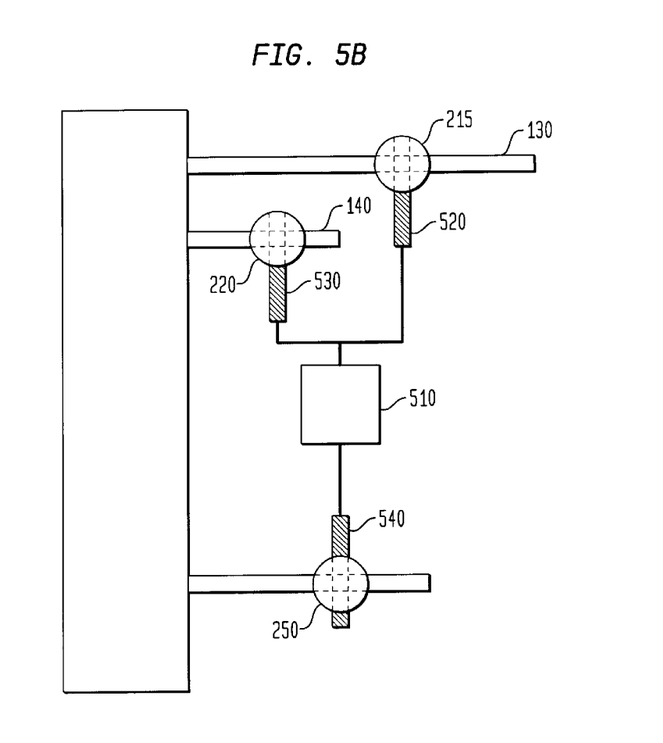

FIG. 5b illustrates exemplary actuator 510 of FIG. 5a in a second position. In this illustrative second position, solenoids or plungers 520, 530 are positioned in valves 215, 220, respectively, such that fluid flows through valves 215, 220, respectively, and solenoid or plunger 540 is positioned such that fluid flow through valve 250 is prevented.

Although FIGS. 5a and 5b illustrate a mechanical means for concurrently controlling valves 215, 220 250, it will be appreciated that electrical and/or pneumatic means can, and preferably, be used to control the operation of respective valves. For example, electrical motor driven valves may be used to determine the position of each illustrated valve.

Furtherstill, although the operation of valves 215, 220 and 250 has been disclosed in a concurrent sequence, it will be appreciated that each valve may be independently or sequentially operated without altering the scope or operation of the present invention.

Figure 6:
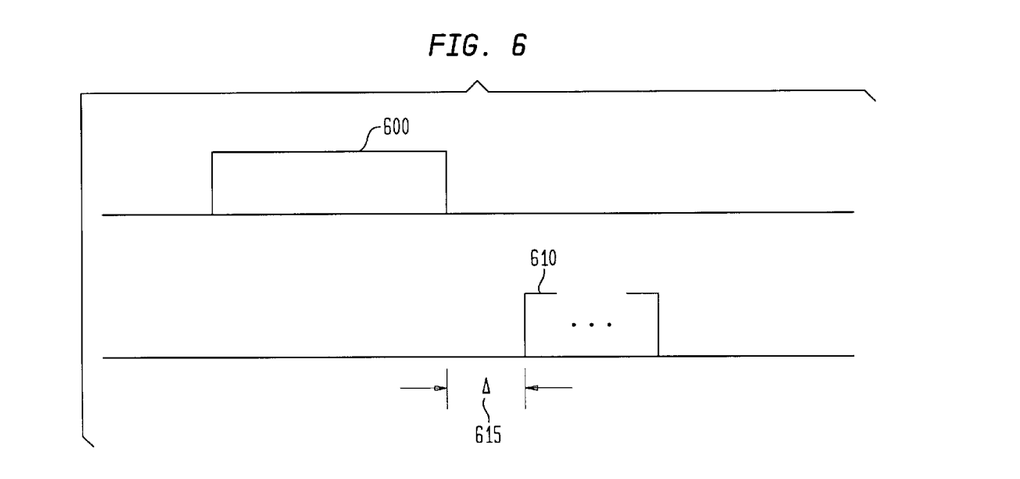
FIG. 6 illustrates an exemplary valve operation timing in accordance with the principles of the invention.

FIG. 6 illustrates an exemplary timing diagram of a sequential valve operation. In this exemplary timing diagram, signal 600 is representative of a motor drive signal that is used to drive actuators that causes valves 215, 220 to transition from an initial state, or position, to a second state or position, e.g., from a fluid flow prevention state to a fluid flow state. Signal 600 is then returned to an initial level and valves 215, 220 are returned to their initial position. After a known period 615, signal 610, which is representative of a motor drive signal, is used to drive actuators that cause valve 250 to transition from an initial known state or position to a second known state or position, e.g., from a fluid flow prevention state to a fluid flow state. After a steady state level of vapor pressure has been measured, valve 250 similarly is returned to its initial position. In this illustrative example, valve 250 transitions to its initial state or position by removing drive signal 610.

As would be appreciated, valves 215, 220, and 250 may also be self-driven to an initial position analogous to a normally-open or normally-closed electrical switch. In this case, the illustrative signals are not used to return a respective valve to an initial position, but rather the lack of a signal, or in the case of negative logic control, the presence of a signal, causes the respective valve to return to an initial position.

It will be appreciated that drive signal 600 may be returned to an initial state after drive signal 610 is activated. In this case, valves 215, 220 are returned to their respective initial known position while valve 250 transitions to a second position.

Although the invention has been described in a preferred form with a certain degree of particularity, it is understood that the present disclosure of the preferred form has been made only by way of example, and that numerous changes in the details of construction and combination and arrangement of parts may be made without departing from the spirit and scope of the invention as hereinafter claimed. In other embodiments, hardware circuitry may be used in place of, or in combination with, software instructions to implement the invention. For example, the elements illustrated herein may also be implemented as discrete hardware elements. It is intended that the patent shall cover by suitable expression in the appended claims, whatever features of patentable novelty exist in the invention disclosed.

We claim:

1. A pressure measurement device in fluid communication with a pumping system for dynamically determining a vapor pressure of a fluid passing through said pumping system, comprising:

valves for diverting a portion of said fluid from said pumping system into a chamber, the valves isolating said diverted fluid in the chamber from said pumping system so as to form an isolated fluid for measuring;

an evacuation pump to evacuate said chamber after an evacuation valve is open; and a pressure gauge to measure said vapor pressure of said isolated fluid in the chamber after said evacuation valve is open.

2. The device as recited in claim 1 further comprising:

a first temperature gauge for measuring fluid temperature in said chamber;

a second temperature gauge for measuring fluid temperature in said pumping system;

a temperature compensation element in said chamber for adjusting temperature of said isolated fluid to be substantially the same as said pump fluid.

3. The device as recited in claim 1 wherein the device comprises a controller for controlling the valves, evacuation pump and pressure gauge in response to an occurrence of a known event.

4. The device as recited in claim 1, wherein at least one valve is operable to transfer fluid from said pump to said chamber, and at least one valve is operable, to evacuate air from said chamber.

5. A vapor pressure measurement device for a pump comprising:

a pump chamber having a feed conduit and a return conduit;

a valves in each of said feed conduit and said return conduit, said valve operable to divert fluid from a pump to said device when each of said valves is in a first position and isolate said diverted fluid from said pump when each of said valves is in a second position;

an evacuation pump in fluid communication with said chamber, said evacuation pump operable to evacuate vapor from said chamber;

an evacuation between said chamber and said evacuation pump operable to isolate said chamber from said evacuation pump when said evacuation valve is in a first position;

a pressure gauge to measure said evacuation valve pressure when said evacuation valve is in a second position.

6. The device as recited in claim 5 further comprising:

a temperature gauge; and a temperature compensation element operable to maintain said diverted fluid at a known temperature.

7. The device as recited in claim 6 wherein said temperature compensation device is selected from the group comprising heater, heat exchanger, fluid cooler, air conditioner.

8. A vapor pressure measurement system for dynamically measuring vapor pressure in a pumping system comprising:

a controllable measurement device comprised of a chamber coupled by a plurality of valves operative to divert fluid from said pumping system and measure said vapor pressure of an isolated pumped fluid in the chamber while said pumping system is operating, an evacuation pump to evacuate said chamber after an evacuation valve is open, and a pressure gauge to measure said vapor pressure of said isolated fluid in the chamber after said evacuation valve is open; and a controller coupled to said controllable measurement device operative to control operation of said controllable measurement device.

9. The system recited in said claim 8, wherein said measurement device further comprises:

at least one valve to divert said pumped fluid from said pump when said at least one valve is in a first position;

a chamber coupled to said at least one valve to store said diverted fluid;

at least one evacuation valve coupled to said chamber and in fluid communication with an evacuation pump, said evacuation pump is operative to evacuate said chamber when said evacuation valve is in a first position; and a pressure measurement gauge.

10. The system as recited in claim 9 further comprising:

a temperature compensation device operable to maintain said diverted fluid at a known temperature.

11. The system as recited in claim 9 wherein said temperature compensation device is selected from the group comprising heater, heat exchanger, fluid cooler, air conditioner.

12. The system as recited in claim 9 wherein said known temperature is representative of a fluid temperature in said pump.

* * * * *

UNITED STATES PATENT AND TRADEMARK OFFICE
CERTIFICATE OF CORRECTION

PATENT NO. : 6,663,352 B2  
APPLICATION NO. : 09/912819  
DATED : December 16, 2003  
INVENTOR(S) : Eugene P. Sabini and Oakley Henyan Page 1 of 1

It is certified that error appears in the above-identified patent and that said Letters Patent is hereby corrected as shown below:

On the title page, item (54) and column 1, line 1

"METHOD AND APPARATUS FOR DYNAMICALLY DETERMINING VAPOR PRESSURE IN PUMPING SYSTEMS" should be --AN APPARATUS FOR DYNAMICALLY DETERMINING VAPOR PRESSURE IN A PUMP, WHEREIN A PORTION OF PUMP FLUID IS DIVERTED USING VALVES AND AN EVACUATION PUMP FOR VAPOR PRESSURE MEASUREMENT--.

In column 6, line 63, claim 5, line 5 "a" should be deleted.

In column 7, line 4, claim 5, line 13 after "evacuation" --valve-- should be inserted.

In column 8, line 13, claim 9, line 11 "; and a pressure measurement gauge" should be deleted.

Signed and Sealed this

Twenty-fifth Day of December, 2007

JON W. DUDAS  
*Director of the United States Patent and Trademark Office*